US00PP23850P2

(12) United States Plant Patent
van Zoest

(10) Patent No.: US PP23,850 P2
(45) Date of Patent: Aug. 27, 2013

(54) ***CLEMATIS* PLANT NAMED 'ZOPRIKA'**

(50) Latin Name: *Clematis*
Varietal Denomination: Zoprika

(75) Inventor: Jan van Zoest, Boskoop (NL)

(73) Assignee: J. Van Zoest Beheer B.V., Boskoop (NL)

( * ) Notice: Subject to any disclaimer, the term of this patent is extended or adjusted under 35 U.S.C. 154(b) by 68 days.

(21) Appl. No.: 13/385,267

(22) Filed: Feb. 10, 2012

(51) Int. Cl.
*A01H 5/00* (2006.01)

(52) U.S. Cl.
USPC ..... Plt./228

(58) Field of Classification Search
USPC ..... Plt./228
See application file for complete search history.

*Primary Examiner* — Annette Para
(74) *Attorney, Agent, or Firm* — Penny J. Aguirre

(57) ABSTRACT

A new cultivar of hybrid *Clematis*, 'Zoprika', characterized by its upright facing tulip-shaped flowers, its flowers that are white and red-purple in color with the upper surface of the tepals white and the lower surface red-purple with white margins, its flowers that retain their color with very little fading, its sterility, and its cold hardiness to at least U.S.D.A. Zone 9.

2 Drawing Sheets

Variety denomination: 'Zoprika'.

BACKGROUND OF THE INVENTION

The present invention relates to a new and distinct cultivar of *Clematis* of hybrid origin (Texensis Group) and will be referred to hereafter by its cultivar name 'Zoprika'. 'Zoprika' is grown as an herbaceous perennial for landscape use or as a flowering potted plant for the terrace.

'Zoprika' is derived from an ongoing breeding program by the Inventor in his nursery in Boskoop, The Netherlands. The goal of the selection was to select a hardy climber with uniquely colored flowers that could be grown for different purposes in the garden. 'Zoprika' was selected as a single unique plant in 2006 and arose from a controlled cross made in 2003 between unnamed plants from the breeding program; the female parent designated as No. 19990039 and the male parent designated as No. 19970052.

Asexual reproduction of the new cultivar was first accomplished by internodial stem cuttings under the direction of the Inventor in Boskoop, The Netherlands in 2006. The characteristics of this cultivar have been determined to be stable and are reproduced true to type in successive generations.

SUMMARY OF THE INVENTION

The following traits have been repeatedly observed and represent the characteristics of the new cultivar as grown outdoors and observed for five years in Boskoop, The Netherlands. These attributes in combination distinguish 'Zoprika' from other varieties of *Clematis* known to the Inventor.

1. 'Zoprika' exhibits upright facing tulip-shaped flowers.
2. 'Zoprika' exhibits flowers that are white and red-purple in color with the upper surface of the tepals white and the lower surface red-purple with white margins, unique in the Texensis Group.
3. 'Zoprika' exhibits flowers that retain their color with very little fading.
4. 'Zoprika' is sterile; no seed is produced.

5. 'Zoprika' is cold hardy to at least in U.S.D.A. Zone 9.

'Zoprika' differs from its female parent in having tulip-shaped flowers while the female parent has spreading flowers. 'Zoprika' differs from its male parent in having much large flowers that are tulip-shaped rather than open.

'Zoprika' can be compared to the cultivars 'Princess Diana' (not patented) and 'Sir Trevor Lawrance' (not patented). Both cultivars are similar in having tulip-shaped flowers. 'Princess Diana' differs from 'Zoprika' in having tepals that are red purple with a thin white margin on both surfaces. 'Sir Trevor Lawrance' differs from 'Zoprika' in having flowers with tepals that are red-pink in color on both surfaces.

BRIEF DESCRIPTION OF THE DRAWING

The accompanying colored photographs illustrate the overall appearance and distinct characteristics of the new *Clematis*. The photographs were taken of a three year-old plant of 'Zoprika' as grown in a one-gallon container in Boskoop, The Netherlands.

The photograph in FIG. 1 shows the flowering habitus.

Figure 1:
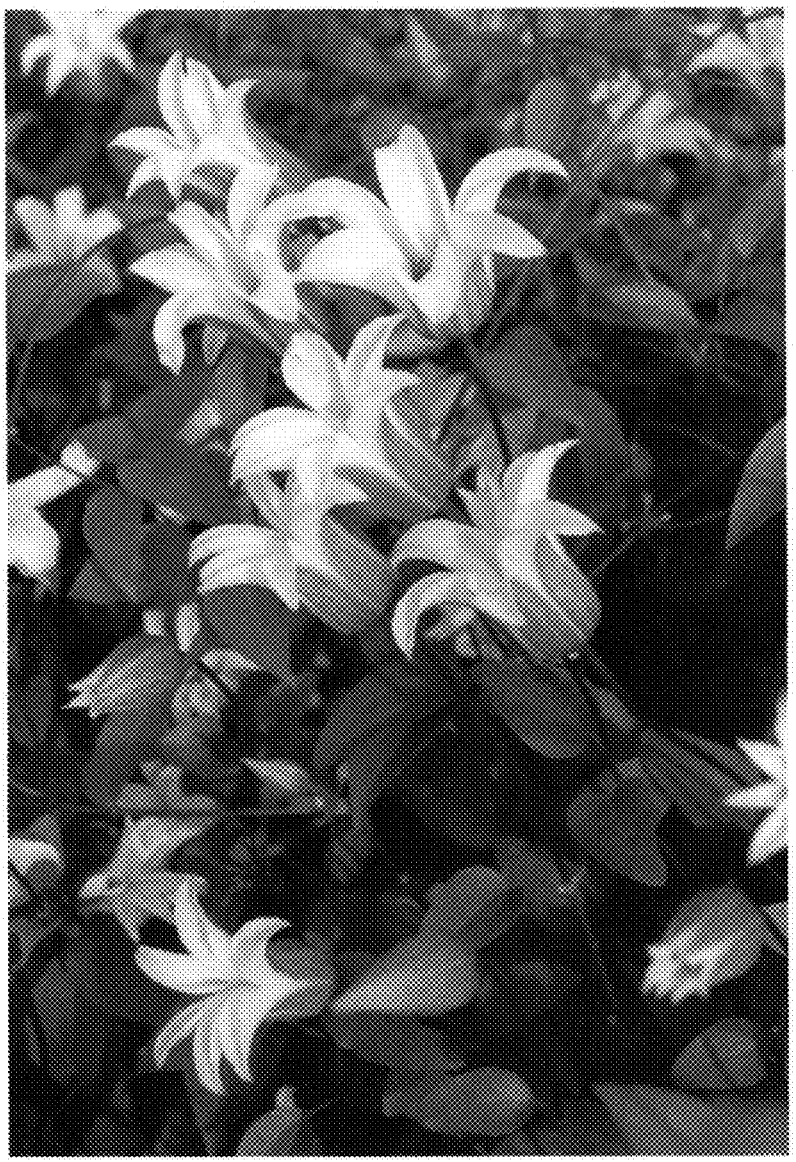
Figure 2:
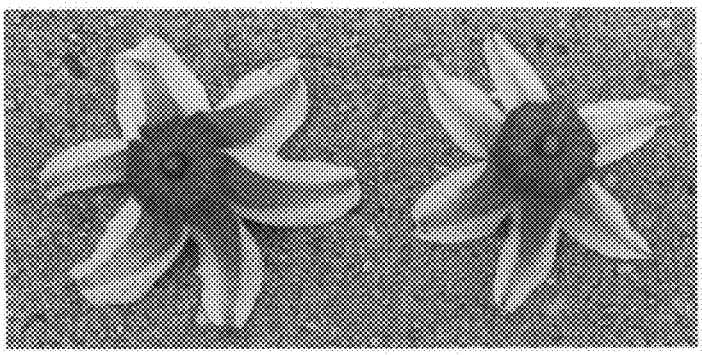

The photograph in FIG. 2 shows the back of the flower.

Figure 3:
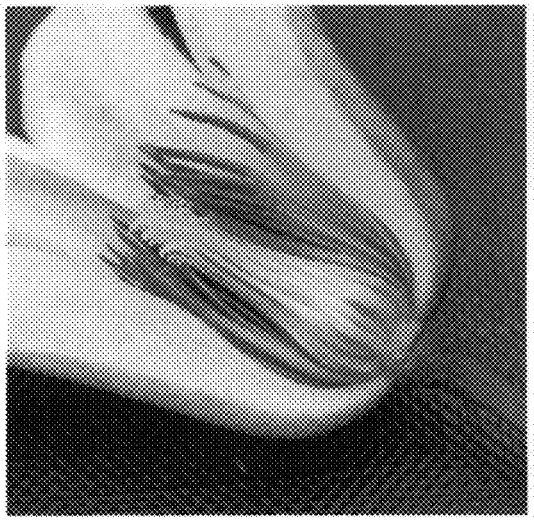

The photograph in FIG. 3 shows the inside of the flower with a close up of the stamens and pistils.

Figure 4:
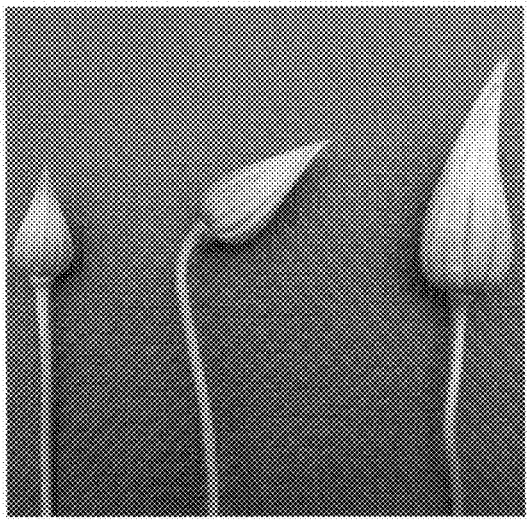

The photograph in FIG. 4 shows the flower buds in different stages.

Figure 5:
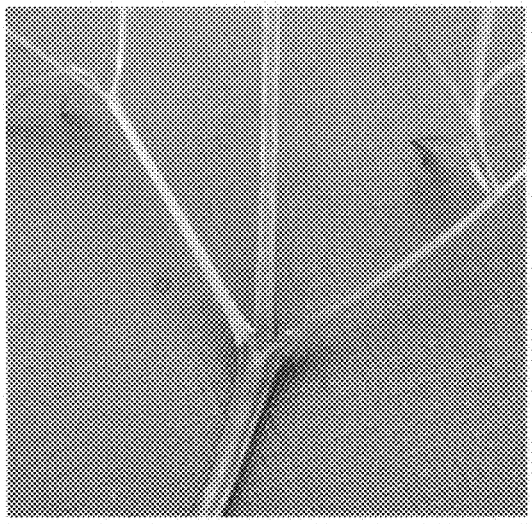
Figure 6:
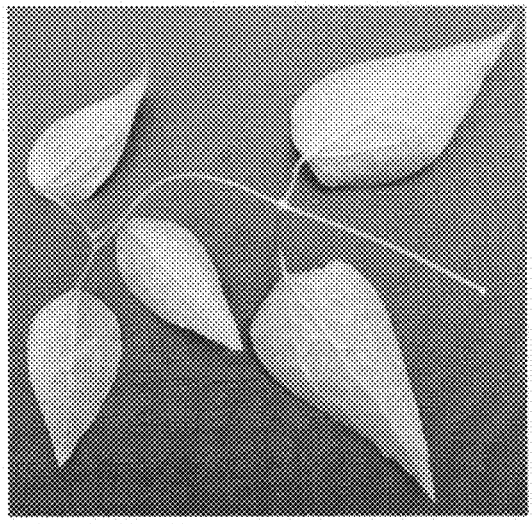

The photograph in FIG. 5 shows part of the stem with a node and the photograph in FIG. 6 shows a leaf.

The colors of the photographs are as close as possible with the digital photography techniques available, the color values cited in the detailed botanical description accurately describe the colors of the new *Clematis*.

DETAILED BOTANICAL DESCRIPTION

The following is a detailed description of three year-old plants of *Clematis* 'Zoprika' as grown outdoors in full sun in one-gallon containers at a nursery in Boskoop, The Netherlands. The phenotype of the new cultivar may vary with variations in environmental, climatic and cultural conditions, as the cultivar has not been tested under all possible environmental conditions. The color determination is in accordance with The 2001 R.H.S. Colour Chart, London, England, except where general color terms of ordinary dictionary significance are used.

General description:

*Botanical classification.*—*Clematis* 'Zoprika' (classified in the Texensis Group).

*Blooming period.*—From late spring to late summer.

*Plant habit.*—Herbaceous climber.

*Height and spread.*—Three year-old plant is about 15 cm in width at the base and 4 m in height when pruned hard in late winter.

*Cold hardiness.*—At least to U.S.D.A. Zone 9.

*Culture.*—Moist but well-drained soils in full sun with the roots shaded.

*Diseases and pests.*—Susceptibility to powdery mildew is unknown.

*Root description.*—Fleshy.

Growth and propagation:

*Propagation.*—Internodial soft wood cuttings from vegetative shoots.

*Root initiation.*—Roots develop in 6 weeks in summer under greenhouse conditions.

*Time required for root development.*—75 to 90 days to develop a 5-cm container from a 5-cm cutting.

*Growth rate.*—Vigorous once planted in the landscape.

Stem description:

*Shape.*—Round and strongly 6-ribbed.

*Stem color.*—Between 172A and 175A in color.

*Stem size.*—About 3 to 4 m in length (including peduncle and terminal pedicel), an average of 2 to 5 mm in diameter.

*Stem surface.*—Glabrous, sparsely covered with hairs.

*Internode length.*—Ranges from 3 to 9 cm.

*Branching.*—Branching from the base and occasionally lateral branches emerge when the basal branches are 1.2 to 3 m in height.

Foliage description:

*Leaf arrangement.*—Opposite.

*Leaf division.*—Pinnate.

*Leaf size.*—Up to 15 cm in length and 11 cm in width.

*Leaf attachment.*—Petiolate.

*Leaflet shape.*—Lanceolate.

*Leaflet base.*—Obtuse.

*Leaflet apex.*—Acuminate.

*Leaflet fragrance.*—Fresh "green" fragrance when crushed.

*Leaflet venation.*—Upper surface slightly reticulate, lower surface reticulate.

*Leaflet margins.*—Entire.

*Leaflet attachment.*—Petiolulate.

*Leaflet surface.*—Upper surface; glabrous, lower surface; surface sparsely covered with short hairs.

*Leaflet size.*—Up to 7 cm in length and 4 cm in width.

*Leaflet color.*—Upper surface; 147A, lower surface; 147B.

*Petioles and petiolules.*—Petiole; 4 to 8 cm in length, 145C flushed with 172A in color, round, surface sparsely covered with short hairs, petiolule; 1 to 2.5 cm in length, 145C flushed with 172A in color, round, surface sparsely covered with short hairs.

Inflorescence description:

*Inflorescence type.*—Solitary or a 3-flowered dichasial cyme.

*Inflorescence arrangement.*—Terminal and axillary on young shoots.

*Peduncles.*—Up to 10 cm in length, 145B flushed with 59A in color, round, surface slightly 6 ribbed, surface sparsely hairy.

*Pedicels.*—Up to 15 cm in length, 59A in color, round and slightly ribbed, surface sparsely hairy becoming more dense towards flower.

*Flower buds.*—First stage is upright followed by a nodding stage and before opening upright again, lanceolate in shape, apex acuminate, base obtuse, 61A in color with a bit 1C at apex.

*Flower fragrance.*—None.

*Lastingness of the flowers.*—Individual flowers last up to about 6 to 10 days until the first tepal drops, followed later by the stamens.

*Flower quantity.*—20 to 50 per stem.

*Flower type.*—Single, tulip-shaped.

*Flower aspect.*—Upright.

*Flower size.*—Average of 4 cm in length and 6 cm in diameter.

*Flower sex.*—Bisexual.

*Tepal number.*—Average of 6.

*Tepal shape.*—Elliptic.

*Tepal apex.*—Acuminate.

*Tepal base.*—Cuneate.

*Tepal margin.*—Entire.

*Tepal surface.*—Inner surface; glabrous, outer surface; sparsely hairy, margin; very short hairs.

*Tepal color.*—Inner surface; 155B in color with slight tint of 84B in cold weather, outer surface middle; shiny, 71A in color but paler toward apex, margin 155A in color.

*Tepal size.*—Up to 5 cm in length and 2 cm in width.

Reproductive organs:

*Gynoecium.*—Average of 30 to 40 pistols, up to 1.3 cm in length, ovary 1C in color with short hairs on surface, style is a blending of 155B and 1C in color and plumose, stigma is 1C in color and reflexed.

*Androcoecium.*—Filaments are 0.5 cm to 0.9 cm in length, 0.08 cm in width and linear in shape, surface is glabrous with a few sparse hairs below the anthers, 59C in color at the base and 145C towards the anthers; anthers are 0.5 cm in length, 1 mm in width and linear in shape, 59C in color with pollen 59D; connective 0.05 cm elongated, apex acute, surface covered with short hairs.

*Seed.*—Sterile, seeds are not produced.

It is claimed:

1. A new and distinct cultivar of *Clematis* plant named 'Zoprika' as herein illustrated and described.

* * * * *